(12) United States Patent
Ausserre et al.

(10) Patent No.: US 10,295,822 B2
(45) Date of Patent: May 21, 2019

(54) METHOD FOR MANUFACTURING CONTRAST AMPLIFYING SUBSTRATES

(71) Applicants: CENTRE NATIONAL DE LA RECHERCHE SCIENTIFIQUE, Paris (FR); UNIVERSITE DU MAINE, Le Mans (FR)

(72) Inventors: Dominique Ausserre, Soulitre (FR); Claude Amra, Marseilles (FR); Myriam Zerrad, Marseilles (FR); Refahi Abou Khachfe, Barja El Chouf (LB)

(73) Assignees: CENTRE NATIONAL DE LA RECHERCHE SCIENTIFIQUE, Paris (FR); UNIVERSITE DU MAINE, Le Mans (FR)

( * ) Notice: Subject to any disclaimer, the term of this patent is extended or adjusted under 35 U.S.C. 154(b) by 190 days.

(21) Appl. No.: 15/030,063

(22) PCT Filed: Oct. 17, 2014

(86) PCT No.: PCT/EP2014/072308
§ 371 (c)(1),
(2) Date: Jun. 9, 2016

(87) PCT Pub. No.: WO2015/055810
PCT Pub. Date: Apr. 23, 2015

(65) Prior Publication Data
US 2016/0282611 A1    Sep. 29, 2016

(30) Foreign Application Priority Data
Oct. 18, 2013 (FR) ..................... 13 60198

(51) Int. Cl.
*G01N 21/01* (2006.01)
*G02B 1/02* (2006.01)
(Continued)

(52) U.S. Cl.
CPC ......... *G02B 27/0012* (2013.01); *G01N 21/01* (2013.01); *G02B 1/02* (2013.01);
(Continued)

(58) Field of Classification Search
CPC ...... G01N 33/54373; G02B 1/10; G02B 1/11; G02B 5/003; G02B 5/285; G02B 21/34; G02B 21/06; G02B 27/0012
(Continued)

(56) References Cited

U.S. PATENT DOCUMENTS

| 5,216,542 A | 6/1993 | Szczyrbowski et al. |
| 5,812,405 A | 9/1998 | Meredith |
| 7,652,762 B2 * | 1/2010 | Ausserre ............ G01J 4/00 356/244 |

FOREIGN PATENT DOCUMENTS

| JP | 51-73453 A | 6/1976 |
| JP | 2002-40238 A | 2/2002 |
| JP | 2005-530169 A | 10/2005 |

OTHER PUBLICATIONS

S. G. Moiseev et al., "Design of Antireflection Composite Coating Based on Metal Nanoparticle," Physics of Wave Phenomena, 2011, vol. 19, No. 1, pp. 47-51.
(Continued)

*Primary Examiner* — Collin X Beatty
(74) *Attorney, Agent, or Firm* — Baker & Hostetler LLP

(57) ABSTRACT

A method for producing a contrast-amplifying support comprising an absorbing substrate carrying at least one absorbing layer comprises a design step for the support and the following steps: i) choosing an illumination wavelength $\lambda$; ii) choosing a material constituting the substrate and exhibiting, at illumination wavelength $\lambda$, a complex refractive index $N0=n0-jk0$ with $k0 \geq 0.01$; iii) choosing an ambient medium in contact with the layer on the side opposite to the substrate and exhibiting, at illumination wavelength $\lambda$, a
(Continued)

complex refractive index $N3=n3-jk3$ with $k3 \geq 0$; iv) determining a nominal complex refractive index $N1=n1-jk1$ and a nominal thickness $e1$ of the layer wherein it behaves in the guize of antireflection layer when illuminated under normal incidence at illumination wavelength $\lambda$; and v) choosing a material constituting the layer and exhibiting, at illumination wavelength $\lambda$, a complex refractive index whose real and imaginary parts coincide with the nominal complex refractive index.

7 Claims, 9 Drawing Sheets

(51) Int. Cl.
| | | |
|---|---|---|
| *G02B 1/11* | (2015.01) | |
| *G02B 27/00* | (2006.01) | |
| *G02B 5/00* | (2006.01) | |
| *G06F 17/50* | (2006.01) | |

(52) U.S. Cl.
CPC ............. *G02B 1/11* (2013.01); *G02B 5/003* (2013.01); *G06F 17/5086* (2013.01); *G01N 2201/068* (2013.01)

(58) Field of Classification Search
USPC .................................................. 359/385, 586
See application file for complete search history.

(56) References Cited

OTHER PUBLICATIONS

Mikhail A. Kats et al., "Nanometre optical coatings based on strong interference effects in highly absorbing media," Nature Materials, vol. 12, No. 1, Oct. 14, 2012, pp. 20-24, XP055122795.

R. M. A. Azzam et al., "Antireflection of an absorbing substrate by an absorbing thin film at normal incidence," Applied Optics, vol. 26, No. 4, Feb. 15, 1987, pp. 719, XP055122812.

Translation of Notice of Rejection issued in Japanese Patent Application No. 2016-548423, dated Aug. 7, 2018.

\* cited by examiner

METHOD FOR MANUFACTURING CONTRAST AMPLIFYING SUBSTRATES

CROSS-REFERENCE TO RELATED APPLICATIONS

This application is a National Stage of International patent application PCT/EP2014/072308, filed on Oct. 17, 2014, which claims priority to foreign French patent application No. FR 1360198, filed on Oct. 18, 2013, the disclosures of which are incorporated by reference in their entirety.

FIELD OF THE INVENTION

The invention pertains to a method for manufacturing contrast-amplifying supports.

The invention is able to be applied to various technical fields, such as biology (detection of biomolecules or microorganisms, observation of cell cultures), nanotechnologies (viewing of nano-objects, such as nanotubes), microelectronics, materials science, etc.

BACKGROUND

The use of antireflection layers (or "λ/4" layers) to increase the optical contrast of an object observed by reflection optical microscopy is a very powerful technique that has been known for many years; in particular, it allowed the first observation of molecular walks by Langmuir and Blodgett in 1937 and, more recently, the viewing of graphene layers by Novoselov et al.

Let I be the luminous intensity reflected by the object to be observed, deposited on a support, and $I_s$ that reflected by the support alone; then, the contrast with which the sample is observed equals $C=(I-I_s)/(I+I_s)$. It is understood that the absolute value of this contrast takes its maximum value (equal to 1) when $I_s=0$, that is to say when the support has zero reflectivity, or else when the supported object has zero reflectivity. In the simplest case, the condition $I_s=0$ is satisfied by using in the guise of support a transparent substrate on which is deposited a thin layer, likewise transparent, whose thickness and refractive index are chosen in an opportune manner. In the case of a single antireflection layer, illuminated under normal incidence with a transparent and semi-infinite incident medium (from which the illumination originates) and a transparent and semi-infinite emergent medium (the substrate), the following conditions are obtained:

$$n_1^2 = n_0 n_3 \quad (1a)$$

$$n_1 e_1 = \lambda/4 \quad (1b)$$

where $n_1$ is the refractive index (real) of the layer, $n_0$ and $n_3$ the refractive indices (also real) of the incident and emergent media, $e_1$ the thickness of the layer and λ the illumination wavelength.

For given incident and emergent media, equation (1a) determines in a one-to-one manner the refractive index of the antireflection layer. Unfortunately, this index might not correspond to a commonly used material or one which satisfies diverse constraints related to the application specifically considered. For example, in the case of an air-glass interface—the practical interest of which is obvious—we obtain $n_1 \cong 1.27$, thus requiring the use of composite materials such as aerogels.

SUMMARY OF THE INVENTION

The invention is aimed at overcoming this drawback of the prior art.

To achieve this, the invention proposes to use absorbing antireflection layers, exhibiting a complex refractive index. The extra degree of freedom associated with the presence of an imaginary part of the index makes it possible to relax the constraint bearing on the value of its real part. Moreover, whilst it is difficult to modify the real part of the refractive index of a material, it is relatively simple to modify its imaginary part (for example, by introducing absorbing or diffusing impurities, the diffusion "simulating" absorption).

It should be noted that—in the case of the conventional "λ/4" layers—the increase in the contrast results from an interferential effect which involves multiple reflections at the incident medium/layer interface and layer/emergent medium interface. Now, the absorption of light inside the layer tends to remove the interference between these multiple reflections. Consequently, the very concept of an "absorbing antireflection layer" seems at first sight contrary to intuition.

The paper by S. G. Moiseev and S. V. Vinogradov "Design of Antireflection Composite Coating Based on Metal Nanoparticle", Physics of Wave Phenomena, 2011, Vol. 10, No. 1, pages 47-51 studies the conditions that must be satisfied by a weakly absorbing thin layer deposited on a transparent substrate in order to cancel the reflection under normal incidence at the air-substrate interface, the illumination being performed through the air. This document also describes an absorbing thin layer made of composite material containing metallic nanoparticles satisfying these conditions approximately. This layer reduces the reflection at the air-substrate interface, but does not cancel it totally. Furthermore, its manner of operation has been demonstrated—by an analytical study limited to materials with very weak absorption, but this result is difficult to generalize. Moreover, such a coating is not intended to achieve a contrast-amplifying support.

The following papers:

M. A. Kats et al. "Nanometer optical coatings based on strong interference effects in highly absorbing media", Nature Materials, Vol. 12, January 2013, pages 20-24; and R. M. A. Azzam et al. "Antireflection of an absorbing substrate by an absorbing thin film at normal incidence", Applied Optics, Vol. 26, No. 4, pages 719-722 (1987)

disclose absorbing antireflection layers deposited on substrates which are also absorbing. Here again, only particular cases are described, which are difficult to generalize. Furthermore, in the case of the paper by M. A. Kats et al., the removal of the reflection is merely partial.

Document U.S. Pat. No. 5,216,542 discloses an antireflection coating for a glass substrate comprising, on a front face (intended to be illuminated) of the substrate, a multilayer structure comprising transparent layers and absorbing layers of $TiN_x$ and, on a rear face of said substrate, a single absorbing layer of $TiN_x$ whose thickness is not, however, of such a nature as to ensure zero reflectivity, but only low. Such a coating is not intended to achieve a contrast-amplifying support.

In accordance with the invention, the contrast-amplifying support comprises a substrate which is also absorbing. Such a configuration is particularly appropriate for applications in microelectronics. In contradistinction to the aforementioned papers by M. A. Kats et al. and by R. M. A. Azzam et al., the invention makes it possible to produce an absorbing antireflection layer suitable for any absorbing substrate, in the presence of any incident medium—absorbing or transparent.

Moreover, absorbing antireflection layers such as described hereinafter may also be appropriate for applications other than contrast amplification—in fact, whenever one wishes to remove or attenuate the reflection of light between an absorbing substrate and a transparent or absorbing ambient medium, in the presence of illumination originating from said ambient medium.

A subject of the invention is therefore a method for producing a contrast-amplifying support comprising an absorbing substrate carrying at least one absorbing layer, said method comprising a design step for said support and a step of hardware production of the support in accordance with said design step, characterized in that said design step comprises the following steps:

i) choosing an illumination wavelength λ;
ii) choosing a material constituting said substrate and exhibiting, at said illumination wavelength λ, a complex refractive index $N_0=n_0-jk_0$, where $k_0 \geq 0.01$ and preferably $k_0 \geq 0.01$;
iii) choosing an ambient medium in contact with said layer on the side opposite to said substrate and exhibiting, at said illumination wavelength λ, a complex refractive index $N_3=n_3-jk_3$, where $k_3 \geq 0$;
iv) determining a nominal complex refractive index $N_1=n_1-jk_1$ and a nominal thickness $e_1$ of said layer which are such that it behaves in the guise of antireflection layer when it is illuminated under normal incidence at said illumination wavelength λ; and
v) choosing a material constituting said layer and exhibiting, at said illumination wavelength λ, a complex refractive index whose real and imaginary parts coincide with those of said nominal complex refractive index at least by a tolerance of less than or equal to 5%, and preferably less than or equal to 0.3%;

in which, during said step iv), said nominal complex refractive index and said nominal thickness are chosen satisfying the following conditions:

a) $$v_1^2 = 1 + \kappa_1^2 + \frac{(\kappa_3 - \kappa_0)}{(a_{03} - 1)}[2\sqrt{\alpha_{03}}\, v_1\kappa_1 - \alpha_{03}\kappa_3 - \kappa 0 - \kappa 0\kappa 3$$

b) $$\delta_1 = \frac{a_{03} - 1}{2v_1\kappa_1 - \sqrt{\alpha_{03}}\,\kappa_3 - \sqrt{\frac{1}{\alpha_{03}}}\,\kappa_0}$$

c) $\kappa_1 \leq v_1$, and d) $k_1 \geq 0.15$ where $$\delta_1 = \frac{2\pi n_0}{\lambda} e_1;$$

$$v_1 = \frac{n_1}{\sqrt{n_0 n_3}};$$

$\alpha_{03} = n_0/n_3;$ and $$\kappa_i = \frac{k_i}{\sqrt{n_0 n_3}} \text{ for } i = 0, 1, 3.$$

Said absorbing layer can be made of a conducting material such as a metal, and said substrate be made of a semi-conducting material. Or, conversely, can be made of a semi-conducting material and said substrate be made of a conducting material such as a metal.

Conventionally, it will be considered that a material is transparent to a wavelength λ when the imaginary part of its refractive index at this wavelength is less than 0.01, or indeed than 0.001, or indeed than 0.0001.

BRIEF DESCRIPTION OF THE DRAWINGS

Other characteristics, details and advantages of the invention will emerge on reading the description given with reference to the appended drawings which are given by way of example and which represent, respectively.

DETAILED DESCRIPTION

Figure 1:
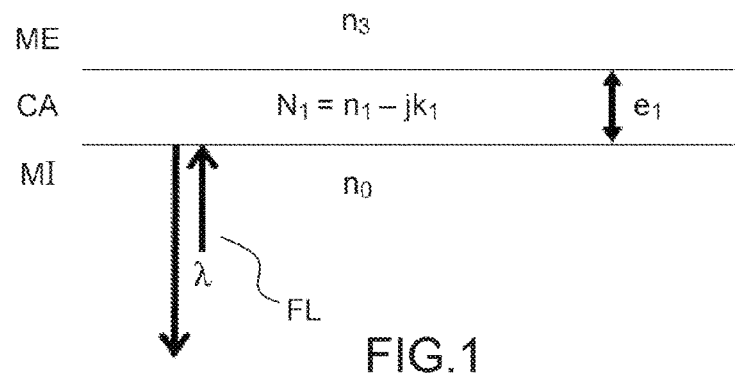
FIG. 1, a structure consisting of a thin layer between two semi-infinite media.

FIG. 1 illustrates a parallel light beam FL (that may be regarded locally as a plane wave) monochromatic at a wavelength (in vacuo) λ, under normal incidence on a structure consisting of: a so-called incident semi-infinite medium MI, from which the light beam originates, which is transparent and characterized by a real refractive index $n_0$; an absorbing layer CA of thickness $e_1$, characterized by a complex refractive index $N_1=n_1-jk_1$ ("j" being the imaginary unit); and a so-called emergent semi-infinite medium ME, situated on the side of the layer opposite to that from which the light originates, which is transparent and characterized by a real refractive index $n_3 < n_0$. The incident medium can in particular be a substrate, for example made of glass, on which the layer CA is deposited. A sample (not represented) of real refractive index $n_2$—or of complex refractive index $N_2=n_2-jk_2$—can be deposited on the layer CA, on the side of the emergent medium. As was explained above, so as to maximize the contrast with which the sample is observed, it is necessary to cancel the reflectance of the incident medium MI/layer CA/emergent medium ME assembly in the absence of sample.

The complex reflection coefficient of a structure of the type illustrated in FIG. 1 (layer of thickness $e_1$ lying between two semi-infinite media) is given by the Airy formula:

$$r_{013} = \frac{r_{01} + r_{13}e^{-2j\beta_1}}{1 + r_{01}r_{13}e^{-2j\beta_1}} \qquad (2)$$

where $r_{ij}$ is the Fresnel coefficient at the interface i–j (j=0, 1 or 3, "0" corresponding to the incident medium, "1" to the layer CA and "3" to the emergent medium) and $\beta_1=2\pi n_1 e_1 \cos\theta_1/\Delta$ is the phase factor associated with said layer, $\theta_1$ being the angle of refraction in the layer. Initially, a transparent layer of real index $n_1$ is considered, the generalization in the case of an absorbing layer will be dealt with further on. Still initially, an incidence which may not be normal is considered.

The Fresnel coefficients for the "p" (TM) and "s" (TE), polarizations are:

$$r_{ij}^{(p)} = \frac{(n_j \cos \theta_i - n_i \cos \theta_j)}{(n_j \cos \theta_i + n_i \cos \theta_j)}$$

and $$r_{ij}^{(s)} = \frac{(n_i \cos \theta_i - n_j \cos \theta_j)}{(n_i \cos \theta_i + n_j \cos \theta_j)}$$

The antireflection condition corresponds to $r_{013}=0$ which, in the case of transparent media (real indices), gives two families of solutions:

the so-called "$\lambda/2$" layers, for which $$e_1 = \frac{m\lambda}{(2n_1 \cos\theta_1)}$$

where m is an integer, which exist only if $n_0=n_3$; and the so-called "$\lambda/4$" layers, for which $n_1 e_1=(2p+1)\lambda/4$ (p an integer).

In the case where the medium 1 (layer CA) is absorbing, its refractive index $N_1=n_1-jk_1$ is complex; the angle of refraction—which is then indicated by $\Theta_1$—and the phase coefficient—$B_1$— are also complex. In this case, $r_{013}=0$ requires: $r_{01,s}r_{13,p}=r_{01,p}r_{13,s}$; this equality can only be true if one of the following three conditions: $\Theta_1=0$ (normal incidence), $N_1^2=n_0^2$ (no layer) or $n_0^2=n_3^2$ (identical incident and emergent media) is satisfied. Consequently, in the case of arbitrary extreme media, the antireflection condition can only be satisfied under normal incidence. Knowing that $r_{011,p}=-r_{01,s}$ and that $r_{13,p}=r_{13,s}$, equation (2) becomes:

$$N_1^2 - j\frac{(n_3 - n_0)}{\tan B_1}N_1 - n_0 n_3 = 0 \quad (3)$$

Equation (3) is transcendental and does not admit of an analytical solution. However, it is possible to find solutions corresponding to extreme cases: strongly absorbing layer and weakly absorbing layer.

In the strongly absorbing case, it may be assumed that $e_1 \ll 2$ since the light would not propagate through a very absorbing and thick layer; consequently, $|B_1| \ll 1$ and it is then possible to write, to second order in $B_1$:
$\tan B_1 \cong B_1 = \sqrt{n_3/n_0}(N_1/\sqrt{n_0 n_3})\delta_1$, where $\delta_1=(2\pi n_0/\lambda)e_1$. It is useful to separate the real and imaginary parts of the equation, and to use the "reduced" variables $v_1=n_1/\sqrt{n_0 n_3}$ and $\kappa_1=k_1/\sqrt{n_0 n_3}$. Equation (3) can then be written in the form of the following system:

$$v_1^2 = 1 + \kappa_1^2 \quad (4a)$$

$$\delta_1 = \frac{\left(\frac{n_0}{n_3} - 1\right)}{2v_1\kappa_1} \quad (4b)$$

Given that $\delta_1$ must be real and positive, we have the condition $n_0 > n_3$ ("reversed geometry"). By taking $n_0=1.52$ and $n_3=1.34$—thus corresponding to the glass/water case customarily used in biophotonics—a thickness $e_1=(\lambda/2\pi)(n_0-n_3)/2n_1k_1$ of the order of a nanometer is found, thus confirming the initial assumption. It is interesting—and unexpected—that equation (4a) tends to the conventional index condition as $\kappa_1$—and therefore $k_1$—tends to zero. A comparison with numerical results makes it possible to verify that equation (4a), although derived under the assumption of a strongly absorbing layer, is approximately valid for any value of $k_1$. On the other hand, the value of $e_1$ obtained on the basis of equation (4b) does not tend to $\lambda/4n_1$; consequently, equation (4b) does not have general validity.

In the weakly absorbing case we put $B_1=\pi/2-\varepsilon_1$ (where $\varepsilon_1$ is a complex variable), thus implying:

$$\varepsilon_1 = \pi/2 - \sqrt{\frac{n_3}{n_0}}(v_1 - j\kappa_1)\delta_1.$$

It is then possible to write, to second order in $\kappa_1$:

$$v_1^2 = 1 + \frac{\pi}{2}\sqrt{\frac{n_3}{n_0}}\left(\frac{n_0}{n_3} - 1\right)\kappa_1 - 3\kappa_1^2 + o(\kappa_1^3) \quad (5a)$$

$$\delta_1 \cong \frac{\pi}{2}\sqrt{\frac{n_0}{n_3}}\frac{1}{v_1}\left\{1 - \frac{4}{\pi}\frac{\sqrt{n_0/n_3}}{(n_0/n_3 - 1)}\kappa_1 + \kappa_1^2 + o(\kappa_1^3)\right\} \quad (5b)$$

Figure 2A:
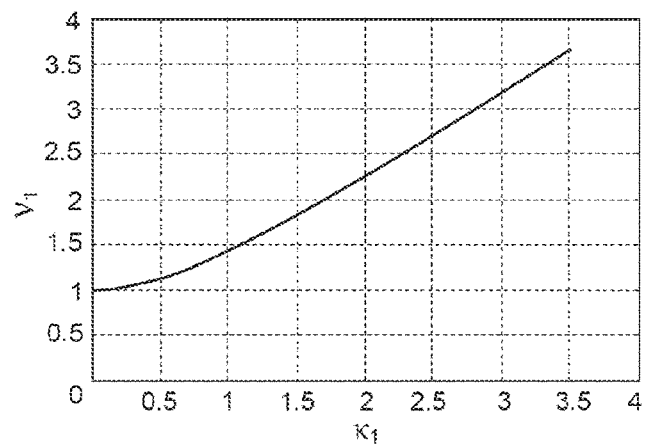
FIGS. 2A to 2D, graphs illustrating the relation between the real and imaginary parts of the refractive indices of absorbing antireflection layers.
Figure 2B:
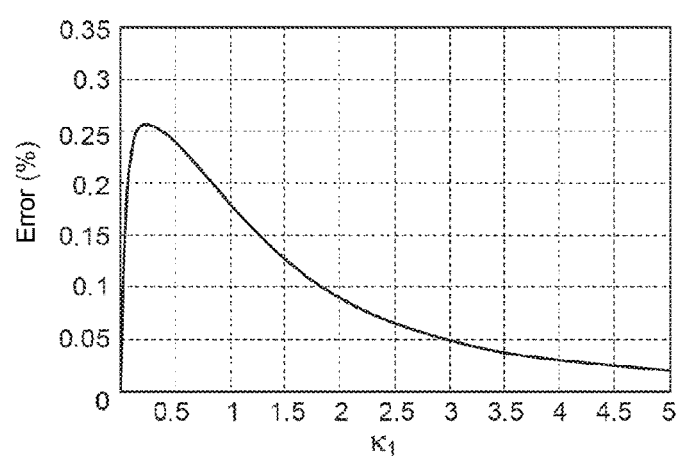
Figure 2C:
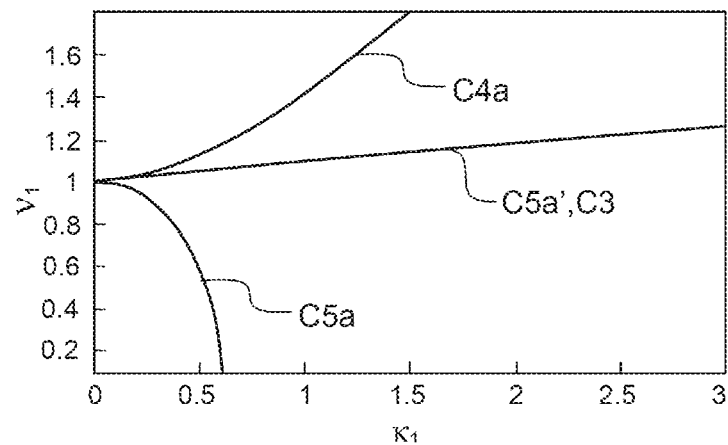
Figure 2D:
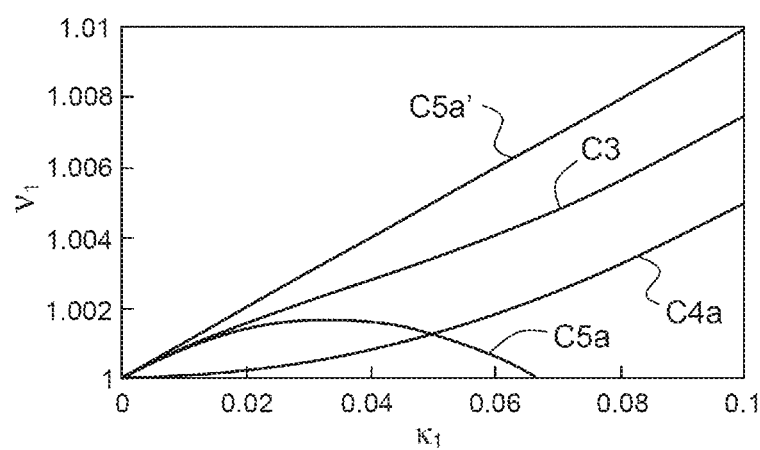

In practice, equation (5a)—whose domain of validity turns out to be very restricted—is of little interest since, as mentioned above, equation (4a) constitutes a satisfactory approximation for any value of $k_1$. This is illustrated by FIG. 2A, which shows the relation $v_1(\kappa_1)$; the curves corresponding to a numerical solution of equation (3) and to equation (4a) cannot be distinguished. FIG. 2B shows the error—as a percentage—of equation (4a) with respect to the numerical solution: it may be seen that this error is very low. FIGS. 2C and 2D are magnifications of FIG. 2A which make it possible to study in greater detail the weak absorption regime; in these figures, curve c4a corresponds to equation (4a), valid for a strong absorption, c3 to the numerical solution of equation (3), c5a to equation (5a) and c5a' to equation (5a) truncated to first order. It may be seen that equation (5a) and its version to first order actually constitute a better approximation than equation 4a for low values of $\kappa_1$, but that equation (4a) remains a fairly good approximation in all cases, while equation (5a) rapidly loses any relevance.

Figure 3A:
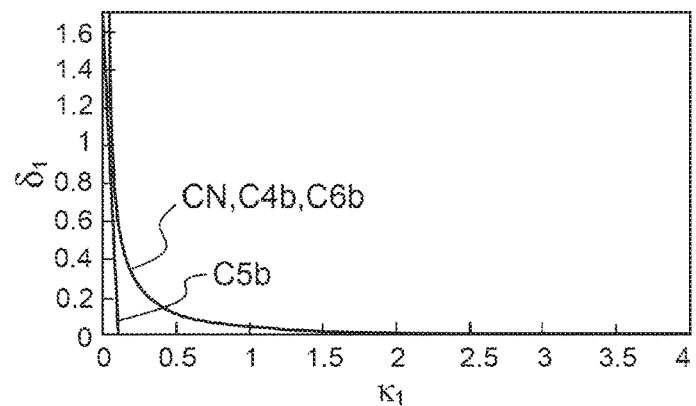
FIGS. 3A to 3C, graphs illustrating the relation between the thicknesses and the imaginary parts of the refractive indices of absorbing antireflection layers.
Figure 3B:
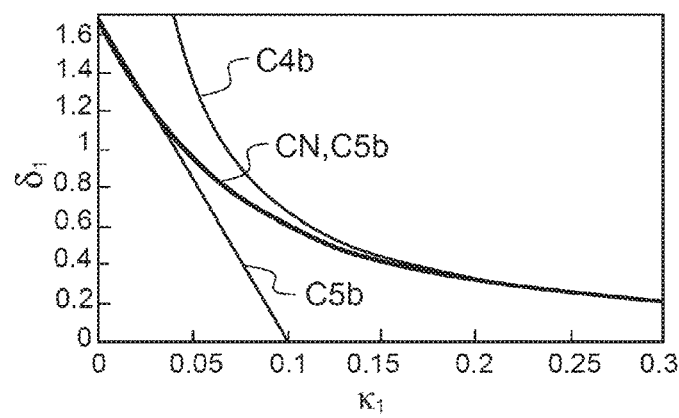
Figure 3C:
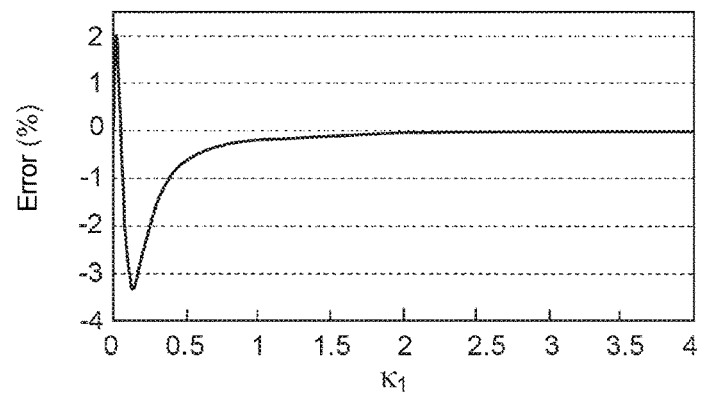

FIGS. 3A and 3B illustrate the relation $\delta_1(\kappa_1)$; the curve cN corresponds to the numerical solution of equation 3, c4b corresponds to equation 4b, valid for large and c5b corresponds to equation 5b. It may be seen that, in this case, the solution obtained for high $k_1$ does not constitute an acceptable approximation for small $\kappa_1$. On the other hand, there exists a semi-empirical equation—corresponding to curve c6b—which turns out to be satisfactory in all cases. FIG. 3C illustrates the error of this semi-empirical solution with respect to the numerical solution: it never exceeds 3.5%. The semi-empirical solution is given by equation 6b hereinbelow; equation 6a is simply equation 4a which, as was shown above, can be considered general and used as replacement for 5b even for small $\kappa_1$:

$$v_1^2 = 1 + \kappa_1^2 \quad (6a)$$

$$\delta_1 \cong \frac{(n_0/n_3 - 1)}{2v_1\kappa_1}\left[1 - e^{-\frac{\kappa_1}{K}}\right] \quad (6b)$$

where $K = \{[\pi/(n_0/n_3-1)]\sqrt{n_0/n_3}\}^{-1}$

Figure 4A:
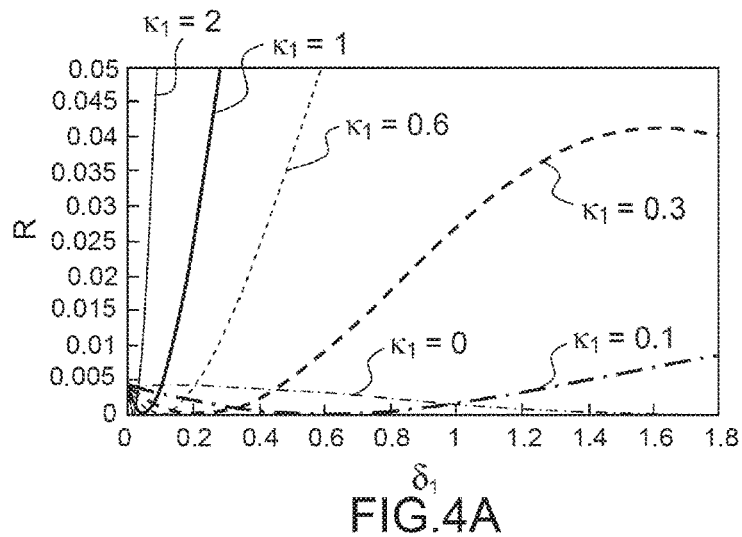
FIGS. 4A to 4F, graphs illustrating the relation between the thicknesses and the reflectances (4A-4D) or absorbances (4E, 4F) of absorbing antireflection layers.
Figure 4B:
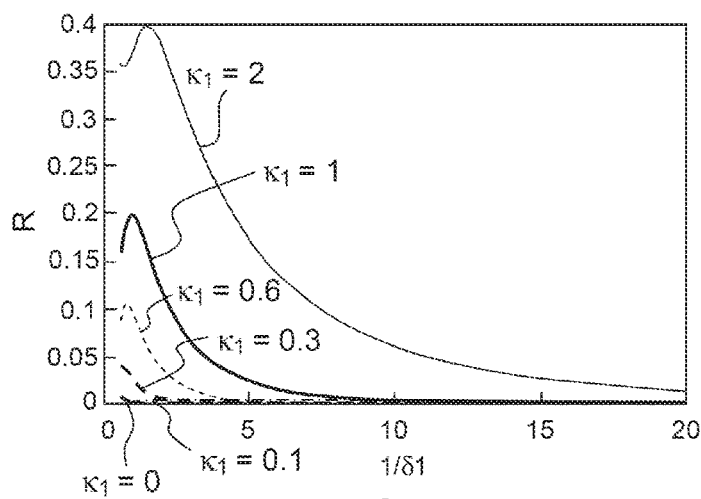

FIG. 4A shows the reflectance curves as a function of $\delta_1$ for various values of $\kappa_1$; FIG. 4B shows the reflectance curves as a function of $1/\delta_1$. As $1/\delta_1$ is proportional to $\lambda$, FIG. 4B illustrates how the reflectance of a given substrate varies as a function of the illumination wavelength. It may be noted that an absorbing antireflection layer dimensioned to operate at a wavelength $\lambda$ attenuates the reflection also at wavelengths $\lambda'>\lambda$. This makes it possible to use these supports under polychromatic illumination also; in the latter case, it is appropriate to perform the dimensioning of the absorbing antireflection layer with respect to the smallest wavelength used for the illumination.

Figure 4C:
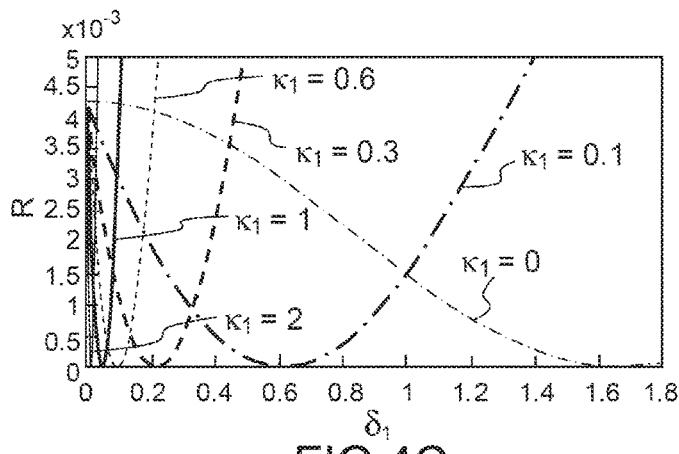
Figure 4D:
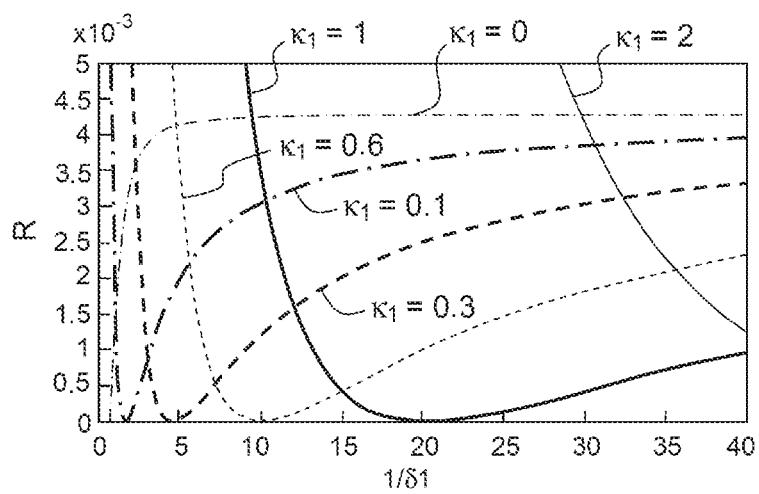
Figure 4E:
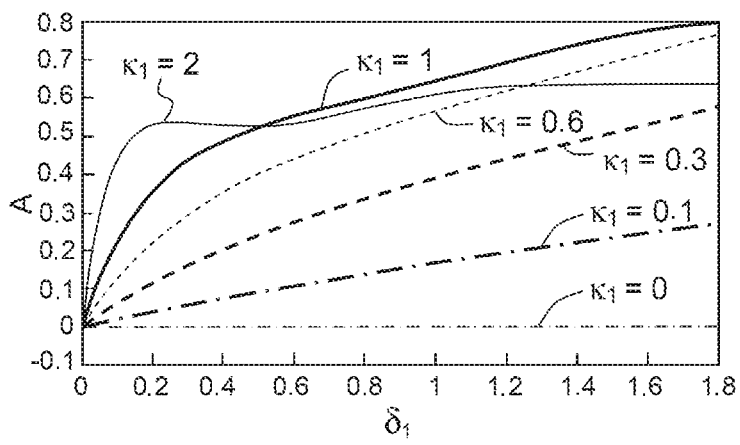
Figure 4F:
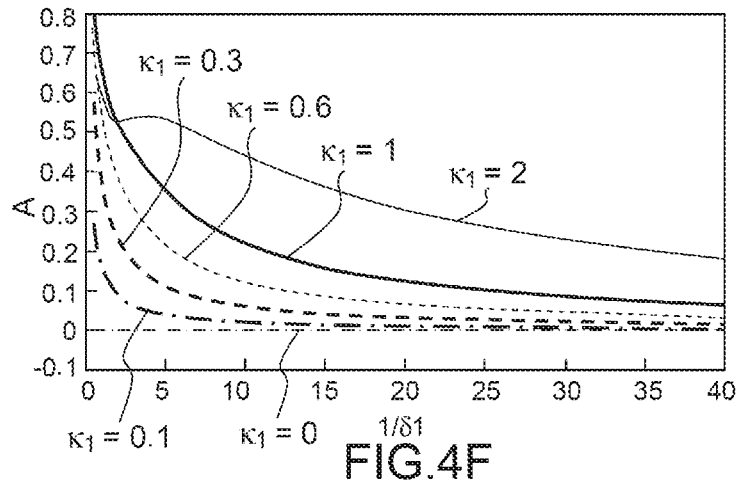

FIGS. 4C and 4D are magnifications of FIGS. 4A and 4B, respectively, showing more specifically the region of the low reflectances. FIGS. 4E and 4F show the absorbance curves for various values of $\kappa_1$, respectively as a function of $\delta_1$ and $1/\delta_1$.

FIGS. 4A to 4D show that the reduced thickness $\delta_1$ of an absorbing antireflection layer is all the lower the more significant the reduced imaginary part $\kappa_1$ of its refractive index. Stated otherwise, the more absorbing the layer, the thinner it must be. Curves 4E and 4F make it possible to verify that the absorbance at the thickness $\delta_1$ given by equation 6b is practically independent of $\kappa_1$ and equals about 0.1.

In their aforementioned paper, G. Moiseev and S. V. Vinogradov have studied an absorbing antireflection layer used in a non-reversed configuration (illumination originating from the medium of lower index); they have found a thickness all the larger the higher the imaginary part of the refractive index of the layer, leading to an absorbance which increases rapidly with the latter. Under these conditions, the ANtiReflection layer can only exist for very low values of $k_1$ it would not be possible to use a very absorbing antireflection layer in the guise of contrast-amplifying layer. This problem does not arise in the case considered here.

Figure 5A:
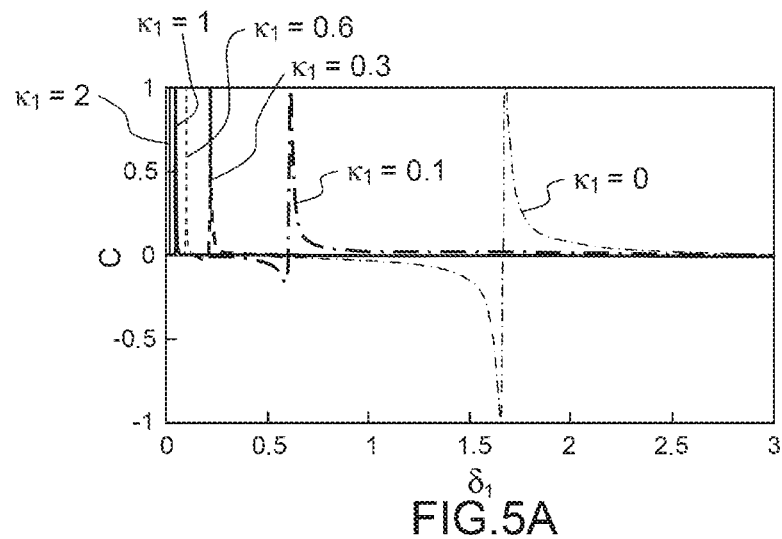
FIGS. 5A and 5B, graphs illustrating the contrasts of observation of a sample, which are obtained by virtue of supports comprising absorbing antireflection layers.
Figure 5B:
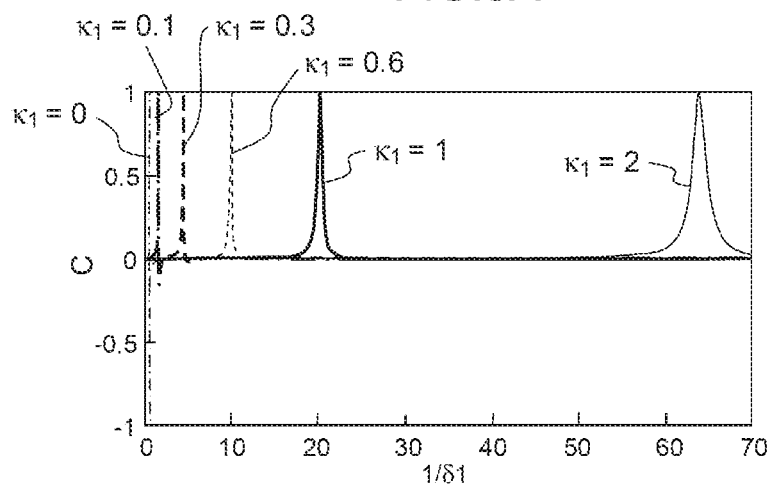

FIGS. 5A to 5D make it possible to study the contrast with which a sample can be observed by virtue of supports comprising an absorbing antireflection layer such as described hereinabove. We consider a glass substrate, an emergent medium consisting of water ($n_0/n_3=1.14$) and a sample consisting of a transparent layer of refractive index $n_2=1.46$. FIG. 5A shows the value of the contrast C with which a sample of thickness $e_2=1$ nm is observed, as a function of the reduced thickness $\delta_1$ for the same values of $\kappa_1$ as those considered in FIGS. 4A-4F: $\kappa_1=0$ (non-absorbing antireflection layer, not forming part of the invention); 0.1; 0.3; 0.6; 1 and 2. FIG. 5B shows the value of this contrast as a function of $1/\delta_1$.

We note that:
only the non-absorbing layer allows a genuine inversion of the contrast (dark sample on bright background); the layer $\kappa_1=0.1$ allows such an inversion but only at a very low contrast level;
the width of the contrast spikes is all the lower—and therefore the tolerance on the reduced thickness of the antireflection layer—the higher is $\kappa_1$. In the case of an object to be observed having a thickness of 1 nm, for $\kappa_1=0.1$ the contrast remains acceptable (0.4) even when $\delta_1$ deviates by ±10% from its optimal value, but it is difficult for this tolerance to exceed 1% for $\kappa_1=1$.

Figure 5C:
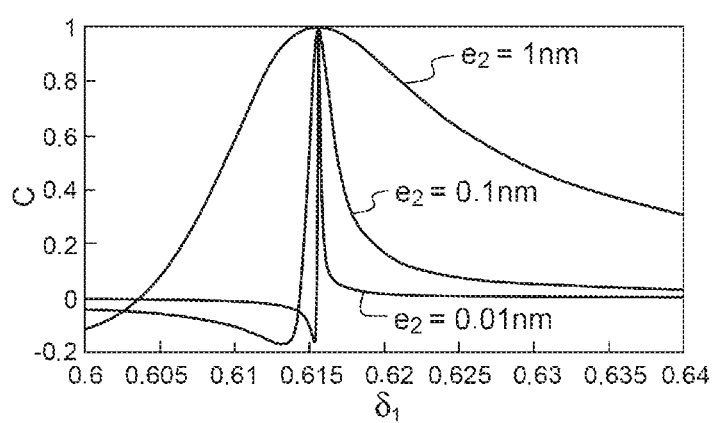
FIGS. 5C and 5D, graphs illustrating the contrasts of observation of samples of different thicknesses, which are obtained by virtue of a support comprising an absorbing antireflection layer.
Figure 5D:
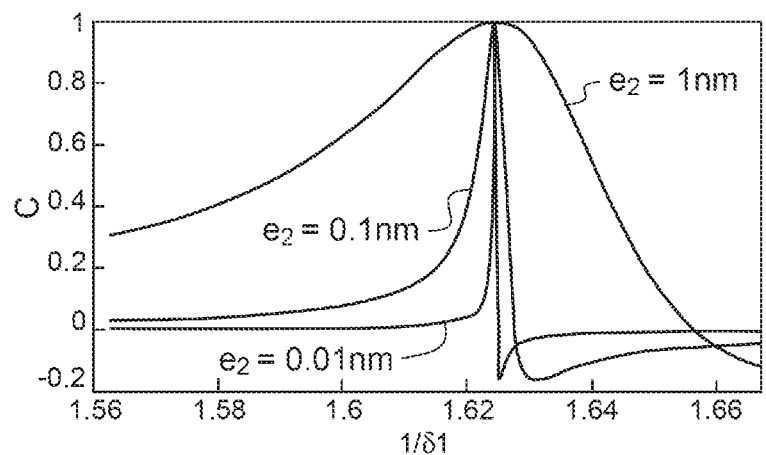

FIGS. 5C and 5D make it possible to study the influence of the thickness of the sample: they show the value of the contrast C as a function of $\delta_1$ and of $1/\delta_1$ respectively, in the case $\kappa_1=0.1$ and for $e_2=1$ nm, 0.1 nm and 0.01 nm (these are effective thicknesses of samples that may consist of sparse atoms or molecules, disposed on the surface of the contrast-amplifying layer). We note that the contrast C can always reach a value of 1, but that the tolerance on $\delta_1$ is all the more reduced the lower the thickness $e_2$. Specifically, as $\delta_1$ depends as much on the thickness of the absorbing antireflection layer as on the illumination wavelength, in the case of very fine samples it may be advantageous to finely adjust this wavelength to maximize the contrast.

It can also be advantageous to choose an illumination wavelength and/or a thickness of the absorbing antireflection layer such that $\delta_1$ is slightly greater than its optimal value, so that the contrast becomes a monotonic function of the thickness of the object, thereby allowing the mapping thereof.

Figure 6:
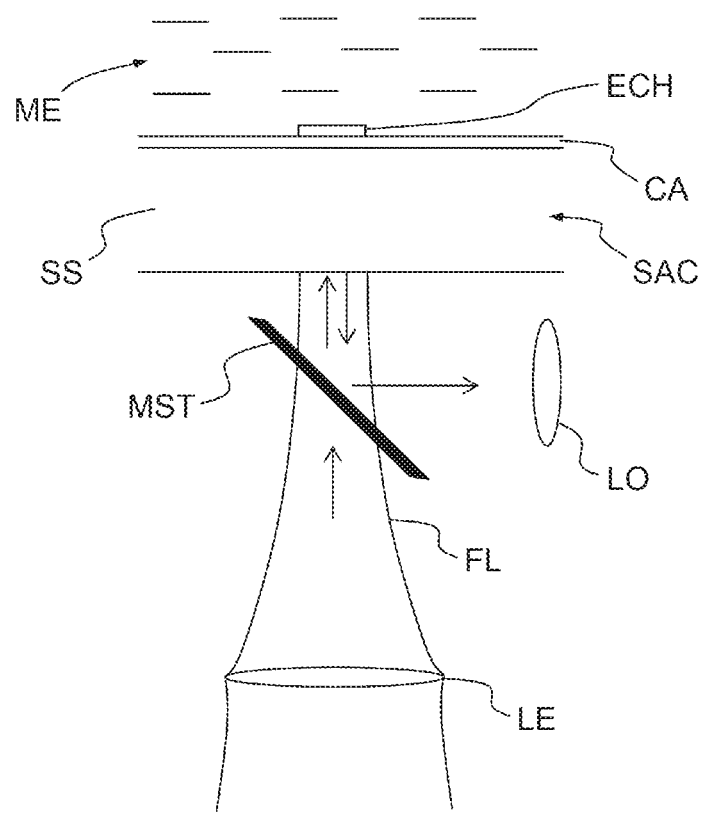
FIG. 6, an application of a contrast-amplifying support comprising an absorbing antireflection layer.
Figure 7A:
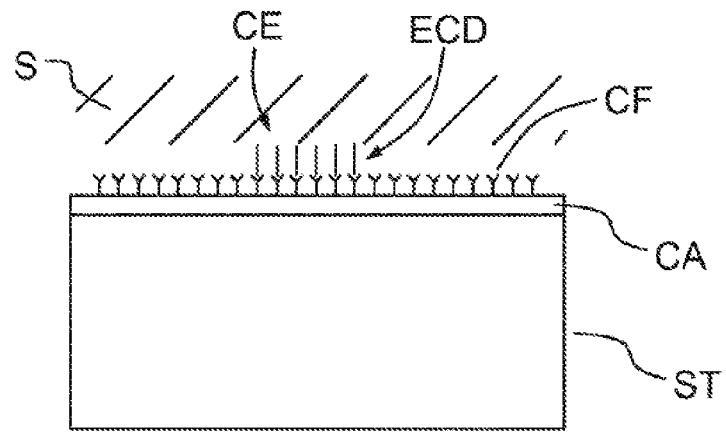
FIGS. 7A to 7E, methods for detecting or assaying at least one chemical or biological species.

FIG. 6 represents a contrast-amplifying support SAC comprising a transparent substrate SS—made for example of glass—serving as incident medium, an antireflection absorbing layer CA deposited on said substrate and in contact with an emergent medium ME, for example an aqueous solution or air. A sample ECH is deposited on a portion of the layer CE, on the side of the emergent medium. The substrate is illuminated under normal incidence by a light beam FL which is, in the example considered here, a laser beam with Gaussian profile, focused by a lens LE at the level of the antireflection layer. It is indeed known that, in its focal region ("beam waist"), a Gaussian beam exhibits a plane phase front, and can therefore be regarded locally as a plane wave (case considered in the foregoing theoretical developments). A semi-transparent mirror MST deviates a portion of the light reflected by the substrate SS/layer CA/sample ECH/emergent medium ME assembly, to direct it toward an objective LO, allowing observation of said sample. The observation can be done by scanning or "full field". As a variant, it is been possible to use a parallel light beam or a telecentric viewing system. It should be noted that the spatial coherence of the incident light and its polarization state are of no significance. On the other hand, if it is desired to observe an intensity contrast, it is appropriate to use narrowband illumination; polychromatic illumination leads to a contrast which is not as much of intensity as of color (sample observed with a different color from that of the background and different colors according to the thickness of the sample).

In the setup of FIG. 6, the lenses LO and LE are interchangeable. Moreover, the parasitic reflection on the front face of the substrate can be usefully attenuated by techniques such as: immersion in an oil, the existence of a bevel between the front face and the rear face, spatial filtering, conventional antireflection treatment.

To design a contrast-amplifying support of the type illustrated in FIG. 6 it is possible to proceed in the following manner:

Firstly, the illumination wavelength (or the smallest illumination wavelength, if the illumination is polychromatic) $\lambda$ is determined as a function of the application considered or of various technological constraints.

Thereafter, a first material intended to constitute the substrate and a material intended to constitute the "ambient medium" or "emergent medium" are chosen. Often, the choice of the ambient medium is determined by the application considered (generally an aqueous solution for biological applications); the choice of the material constituting the substrate is dictated by technological considerations and by the constraint $n_3<n_0$ at the wavelength $\lambda$. Often, a glass substrate will be chosen, together with an ambient medium consisting of air (ratio $n_3/n_0$ lying between 1.45 and 1.7) or water (ratio $n_3/n_0$ lying between 1.1 and 1.3).

Next, equation 6a is used to determine the relation linking the real part and the imaginary part of the refractive index of the material constituting the absorbing antireflection layer. A material satisfying this relation is then chosen—or designed. For example, it is possible to choose a transparent starting material as a function of diverse technological considerations—for example a polymer; take the real part of its refractive index as an imposed datum; and modify the imaginary part of said refractive index by adding impurities (dyes, nanoparticles . . . ) so that equation 6a is satisfied.

Finally, the thickness of said layer is determined by applying equation 6b (or one of equations 4b or 5b, which constitute particular cases thereof).

Thereafter, the production of the support is undertaken by conventional techniques, such as spin coating, immersion coating, roll coating, coating by sedimentation or by evaporation; chemical or physical vapor deposition, ion implantation, electrolytic deposition, etc.

The absorbing antireflection layer can be metallic (and in particular gold), semi-conducting, non-metallic conducting, made of polymer containing pigments or dyes, made of inorganic (mineral) material containing color centers, etc. Among the semi-conducting materials suitable for producing absorbing antireflection layers may be mentioned: germanium (for applications in the near ultraviolet (UV), for example at 354 nm), $TiO_2$ (also in the near UV), molybdenum silicide, nickel silicide or titanium silicide (in the visible), tungsten silicide (in the near infrared or in the near UV), zirconium silicide (in the visible or the near UV), tantalum or vanadium (in the visible), etc. It can also contain metallic nanoparticles. It can be magnetic, this being of interest for the study of samples which are also magnetic. The use of conducting layers—metallic or not—makes it possible to apply a controlled potential difference to the sample and/or to carry out "electrochemical imaging" making it possible to study phenomena of electrodeposition, corrosion, catalysis, etc. A particularly interesting variant consists in making a monolithic support, in which the absorbing antireflection layer is a layer of impurities implanted—for example by ion implantation—on the surface of the substrate; such a substrate can be cleaned and reused, with no danger of impairing the layer. An "absorbing" antireflection layer need not necessarily be absorbing in the proper sense: as a variant, it may be a diffusing layer, the diffusion "imitating" absorption and being able likewise to be modeled by a complex refractive index.

A contrast-amplifying substrate such as described hereinabove also allows the production of biochips for the detection and/or assaying of chemical or biological species. For example, as illustrated in FIG. 7, it is possible to deposit a functionalized layer CF on the contrast-amplifying layer CA. This functionalized layer is placed in contact with a solution S, for example aqueous, containing the chemical or biological species to be detected ECD. The latter is fixed by the functionalized layer and forms an additional thin layer CE, constituting the sample to be observed. In practice, in the case of a biochip, several different functionalized pads will be deposited, making it possible to selectively fix different chemical or biological species. By observing the biochip with a microscope, under the conditions described hereinabove, the species that are actually present in the solution can be easily identified. In certain embodiments, one and the same layer can carry out both the chemical function of selective fixing and also the optical function of contrast amplification.

Preferably, outside of the pads it is possible to provide a passivation layer preventing the fixing of any chemical or biological species contained in said solution ("chemical passivation"). It is possible to use for example a polyethylene glycol, a fluorinated polymer, or a fluorinated alkyl, for example functionalized by thiols in the case of gold. This passivation layer can be deposited in the vapor phase or in the liquid phase after the production of the pads. As a variant or supplement, it is possible to use a discontinuous absorbing antireflection layer, present (or exhibiting an optimal thickness) only in correspondence with the pads; one then speaks of "optical passivation".

When one wishes to detect or deposit chemical or biological species, it is also possible to use a substrate provided solely with the functionalized layer CF. In this case, the absorbing antireflection layer consists of those species fixed by said layer CF.

Figure 7B:
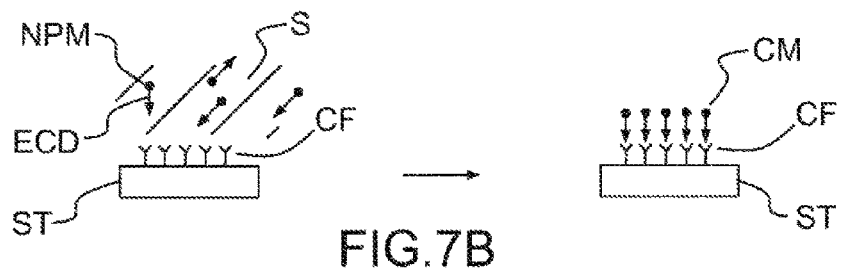
Figure 7C:
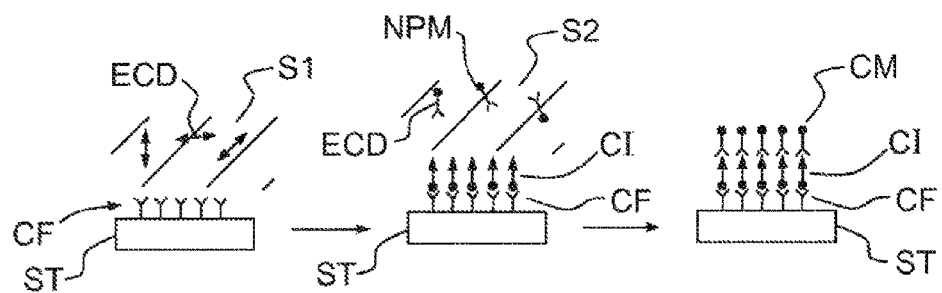
Figure 7D:
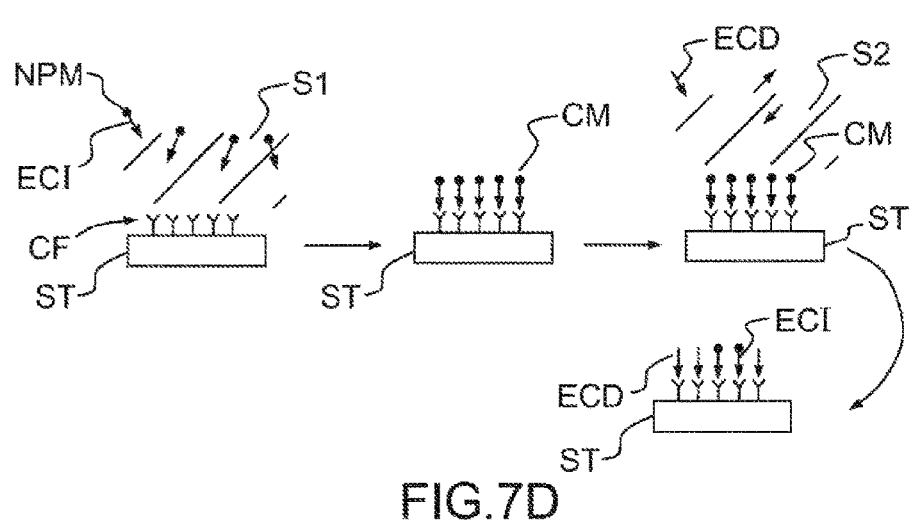
Figure 7E:
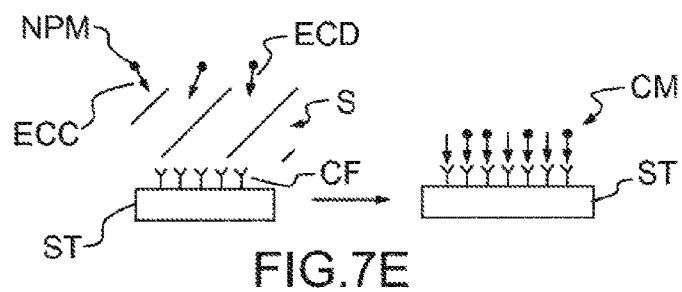

According to a first embodiment, illustrated in FIG. 7B, the functionalized layer is placed in contact with a solution containing a chemical or biological species ECD to be detected or assayed, marked by metallic nanoparticles NPM and able to be fixed on said functionalized layer so as to form a metallic layer CM. This layer may in reality be discontinuous, but it appears continuous on the scale of the wavelength of visible light (several hundred nanometers), with an effective thickness which may be a fraction of the diameter of the nanoparticle, and with an effective refractive index. The observation is made in the manner described above, the metallic layer thus constituted serving both as contrast-amplifying layer and sample. For a determined time of contact between the solution and the functionalized layer, the thickness of the metallic layer depends on the content of chemical or biological species, thereby making it possible to carry out an assay.

As a variant, the metallic nanoparticles can be replaced with an absorbing marker, for example a fluorescent molecule (note that the fluorescence, per se, is not utilized, but a fluorescent molecule is strongly absorbing).

The drawback of the first embodiment is to allow only the detection of a marked chemical or biological species. The following embodiments do not exhibit this drawback.

According to the second embodiment (FIG. 7C), the functionalized layer is placed in contact with a first solution S1 containing the chemical or biological species to be detected or assayed, so as to form a so-called intermediate layer CI. This intermediate layer is not observable. To reveal it, it is placed in contact with a second solution S2, containing a so-called auxiliary chemical or biological species ECA, marked by metallic nanoparticles (or an absorbing marker) and able to be fixed on said intermediate layer so as to form the metallic (or absorbing) layer CM.

The technique can be quantitative if the species to be detected is present in insufficient quantity to saturate the functionalized layer and, on the other hand, the auxiliary species is present in excess. In this case, indeed, the effective thickness and effective index of the layer CM—and therefore the intensity of the observed luminous signal—will depend on the concentration of the species to be detected.

This second embodiment can only be used if the chemical or biological species to be detected exhibits at least two active sites; it does not therefore apply, for example, to haptens. Furthermore, it is fairly complex to implement.

The following embodiments do not exhibit this drawback.

According to the third embodiment (FIG. 7D), the functionalized layer is placed in contact with a first solution (S1) containing a chemical or biological species, the so-called intermediate species ECI, marked by metallic nanoparticles or an absorbing marker and able to be fixed on said functionalization layer so as to form said continuous or discontinuous, metallic or absorbing layer (CM). Thereafter, the assembly thus obtained is placed in contact with a second solution (S2) containing the chemical or biological species to be detected or assayed, which exhibits a greater affinity with said functionalization layer than that of said intermediate species. Thus, the intermediate species is displaced and said metallic or absorbing layer is removed at least in part, this being manifested by an increase in the luminous signal. The technique applies both at a qualitative level to the detection and at a quantitative level to the assaying of the targeted species. An advantage of this approach is that its two steps can be dissociated: the supports can be provided ready to be used as chemical or biological sensors, with the layer CM already formed.

According to a fourth embodiment (FIG. 7E), said functionalized layer is placed in contact with a solution S containing the chemical or biological species to be assayed, as well as said competing chemical or biological species ECC, one of the two species (preferably the competing species) being marked by metallic nanoparticles or an absorbing marker. Thus, a metallic or absorbing layer CM is obtained whose effective thickness and effective index depend on the ratio of the concentration of said competing chemical or biological species to that of said chemical or biological species to be assayed. As in the other embodiments, the signal depends on this effective thickness and on this effective index.

The chemical or biological species can be, for example, antibodies, antigens, proteins, DNA, RNA, saccharides, enzymes, metal ions (in particular for applications to water monitoring), aromatic molecules, organic molecules such as hydrocarbons, microorganisms, etc.

Instead of being metallic or absorbing, the marker can be diffusing. Indeed, as was explained above, the effect of the diffusion can be expressed by a refractive index having an imaginary part. Thus, dielectric nanoparticles such as mineral nanoparticles of silica or of alumina, dendrimers, latex nanoparticles, vesicles, or viruses can play the same role as metallic nanoparticles.

The detection or assaying techniques described hereinabove also apply when the functionalized layer is deposited on a contrast amplification layer such as described above. The functionalized layer, and if appropriate the contrast amplification layer, can be structured as pads, and the surface outside of these pads can be chemically and/or optically passivated, as explained above.

Hitherto we have considered only the case where the illumination and the observation are done through a substrate exhibiting a (real) refractive index which is greater than that of the ambient medium—this being called a "rear face" or "reversed geometry". As a variant, it is also possible to operate in a "front face" configuration, that is to say performing the illumination and the observation through the ambient medium; in this case, the substrate must exhibit a lower refractive index than that of said ambient medium: $n_0 < n_3$.

Another generalization consists in considering an absorbing incident medium and/or emergent medium. The most interesting case is that where the incident medium is transparent and the emergent medium absorbing: indeed, if the incident medium were strongly absorbing, light could not propagate therein to reach the antireflection layer.

Starting from equation (3), in the case $\kappa_1 > 0.15$ and replacing $n_3$ by $N_3 = n_3 - jk_3$ we obtain:

$$v_1^2 - \kappa_1^2 = 1 + \sqrt{\frac{n_0}{n_3}} \kappa_3 \frac{2v_1\kappa_1 - \sqrt{\frac{n_0}{n_3}} \kappa_3}{\left(\frac{n_0}{n_3} - 1\right)} \quad (7a)$$

$$\delta_1 = \frac{\left(\frac{n_0}{n_3} - 1\right)}{2v_1\kappa_1 - \sqrt{\frac{n_0}{n_3}} \kappa_3} \quad (7b)$$

where $\kappa_3 = k_3/\sqrt{n_0 n_3}$.

We remark that, in equation 7b, a high value of $\kappa_3$ can reverse the sign of $\delta_1$. Consequently, it is possible to make an absorbing antireflection layer deposited on a substrate which is also absorbing, illuminated through its face opposite to said substrate ("front face" configuration). It may be for example a metallic layer deposited on a semi-conducting substrate or the converse, this having applications for example in micro-electronics. Layers of this type have been described by the aforementioned paper by R. M. A. Azzam et al. The aforementioned paper by M. A. Kats et al., furthermore, has described layers which are similar but do not totally cancel the reflection. These publications, however, do not provide any general and systematic design process for such layers.

The theory set forth hereinabove makes it possible to design and produce a contrast-amplifying support comprising an absorbing layer deposited on an absorbing substrate as has been described above for the case of a transparent substrate—but by using equations 7a/7b instead of equations 6a/6b.

Figure 8:
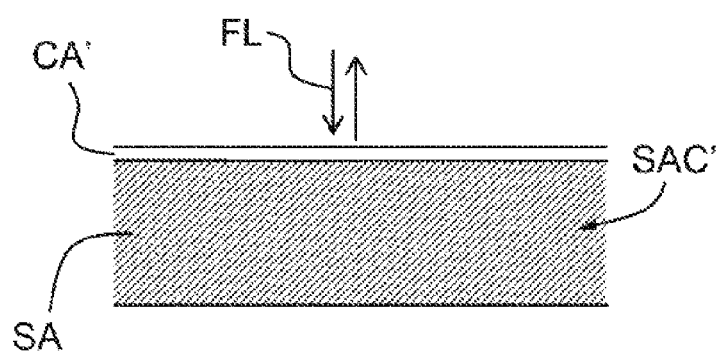
FIG. 8, a contrast-amplifying support according to one embodiment of the invention, implementing an absorbing substrate.

A contrast-amplifying support SAC' of this type, comprising an absorbing substrate SA and an absorbing antireflection layer CA' described by equations 7a and 7b, is represented in FIG. 8. Observation is done "front face" (on the opposite side of the layer from the substrate) by means of a parallel light beam FL, or of a Gaussian laser beam focused as in the case of FIG. 6. The materials mentioned with reference to the layer CA can also be used to make a layer CA'. The latter can also be functionalized or be made with chemical or biological species, optionally marked, fixed by a functionalization layer, in particular for detection or assaying applications.

The invention claimed is:

1. A method for producing a contrast-amplifying support comprising an absorbing substrate carrying at least one absorbing layer, said method comprising a design step for said support and a step of hardware production of the support in accordance with said design step, wherein said design step comprises the following steps:
   i) choosing an illumination wavelength $\lambda$;
   ii) choosing a material constituting said substrate and exhibiting, at said illumination wavelength $\lambda$, complex refractive index N3=n3−jk3, where k3≥0.01;
   iii) choosing an ambient medium in contact with said layer on the side opposite to said substrate and exhibiting, at said illumination wavelength $\lambda$, a real refractive index n0;
   iv) determining a nominal complex refractive index N1=n1−jk1 and a nominal thickness e1 of said layer which are such that it behaves in the guise of antireflection layer when it is illuminated under normal incidence at said illumination wavelength $\lambda$; and v) choosing a material constituting said layer and exhibiting, at said illumination wavelength $\lambda$, a complex refractive index whose real and imaginary parts coincide with those of said nominal complex refractive index at least by a tolerance of less than or equal to 5%;

in which, during said step iv), said nominal complex refractive index and said nominal thickness are chosen satisfying the following conditions:

$$v_1^2 = 1 + \kappa_1^2 + \sqrt{\frac{n_0}{n_3}} \kappa_3 \frac{2v_1\kappa_1 - \sqrt{\frac{n_0}{n_3}}\kappa_3}{\left(\frac{n_0}{n_3} - 1\right)}; \quad \text{a)}$$

$$\delta_1 = \frac{\left(\frac{n_0}{n_3} - 1\right)}{2v_1\kappa_1 - \sqrt{\frac{n_0}{n_3}}\kappa_3}; \quad \text{b)}$$

$$\kappa_1 \leq v_1; \text{ and} \quad \text{c)}$$

$$k_1 \geq 0.15 \quad \text{d)}$$

where $$\delta_1 = \frac{2\pi n_0}{\lambda} e_1;$$

$$v_1 = \frac{n_1}{\sqrt{n_0 n_3}}; \text{ and}$$

$$\kappa_i = \frac{k_i}{\sqrt{n_0 n_3}} \text{ for } i = 0, 1, 3.$$

2. The production method as claimed in claim 1, wherein said absorbing layer is made of a conducting material and wherein said substrate is made of a semi-conducting material.

3. The production method as claimed in claim 1, wherein said absorbing layer is made of a semi-conducting material and wherein said substrate is made of a conducting material.

4. The production method as claimed in claim 1, wherein k3≥0.1.

5. The production method as claimed in claim 1, wherein the tolerance is less than or equal to 0.3%.

6. The production method as claimed in claim 2, wherein the conducting material comprises a metal.

7. The production method as claimed in claim 3, wherein the conducting material comprises a metal.

* * * * *